United States Patent [19]

Eckberg et al.

[11] Patent Number: 5,391,676
[45] Date of Patent: Feb. 21, 1995

[54] SYNTHESES OF EPOXYSILICONES

[75] Inventors: Richard P. Eckberg, Saratoga Springs; Robert F. Agars, Clifton Park, both of N.Y.

[73] Assignee: General Electric Company, Waterford, N.Y.

[21] Appl. No.: 145,451

[22] Filed: Oct. 29, 1993

Related U.S. Application Data

[62] Division of Ser. No. 885,095, May 18, 1992, Pat. No. 5,258,480.

[51] Int. Cl.$^6$ ............................................. C08G 77/08
[52] U.S. Cl. ...................................... 528/15; 556/401; 528/21; 528/27; 528/31
[58] Field of Search .................. 556/401; 528/15, 21, 528/27, 31

[56] References Cited

U.S. PATENT DOCUMENTS

| | | | |
|---|---|---|---|
| 3,867,343 | 2/1975 | Garden | 528/15 |
| 3,928,629 | 12/1975 | Chandra et al. | 427/387 |
| 4,279,717 | 7/1981 | Eckberg et al. | 204/159 |
| 4,421,904 | 12/1983 | Eckberg et al. | 528/27 |
| 4,584,361 | 4/1986 | Janik et al. | 528/32 |
| 4,946,818 | 8/1990 | Lewis | 502/158 |
| 5,158,791 | 10/1992 | Riding | 528/27 |
| 5,173,529 | 12/1992 | Fujiki et al. | 528/15 |
| 5,258,480 | 11/1993 | Eckberg et al. | 528/15 |

OTHER PUBLICATIONS

J. L. Speier, "Homogeneous Catalysis of Hydrosilation by Transition Metals", Advances in Organometallic Chemistry, vol. 17, 407–447, F. G. A. Stone & R. West, eds., Academic Press, 1979.

*Primary Examiner*—Melvyn I. Marquis

[57] ABSTRACT

The invention provides a process for producing epoxyfunctional silicones by a rhodium metal complex-catalyzed hydrosilation reaction between an SiH-containing silane or siloxane and an olefin epoxide, in the presence of a tertiary amine stabilizer. In practicing the invention, $RhCl_3[(CH_3(CH_2)_3)_2S]_3$ or $PtCl_2[(CH_3CH_2)_2S]_2$ are suitable hydrosilation catalysts and methyldicocoamine, $CH_3(C_{18}H_{37})_2N$, is a suitable stabilizer. The invention also provides for a composition including an SiH-functional silane or siloxane, and a tertiary amine, where the composition is not susceptible to gelation during a hydrosilation addition reaction. The invention further provides a method for stabilizing epoxysilicones both during and after the hydrosilation addition reaction used in their production.

9 Claims, No Drawings

SYNTHESES OF EPOXYSILICONES

This is a divisional of application Ser. No. 07/885,095, filed on May 18, 1992, now U.S. Pat. No. 5,258,480.

This application is related to commonly assigned U.S. patent application Ser. No. 07/803,679 filed Dec. 5, 1991, now U.S. Pat. No. 5,227,410 issued Jul. 13, 1993, entitled "UV-Curable epoxysilicone-polyether block copolymers, and U.S. patent application Ser. No. 07/802,681 filed Dec. 5, 1991, now U.S. Pat. No. 5,240,971 issued Aug. 31, 1993, entitled "Improved Syntheses of Epoxysilicones", a division of the aforementioned U.S. Pat. No. 5,227,410, which are incorporated herein by reference.

BACKGROUND OF THE INVENTION

The invention relates to a process for producing epoxy-functional silicones by a hydrosilation reaction between an SiH-functional silane or siloxane and an olefin epoxide, wherein gelation during processing, due to thermally-induced epoxide-mediated crosslinking is eliminated by use of certain rhodium or platinum sulfonium hydrosilation catalysts in combination with a tertiary amine stabilizer. The invention also relates to an epoxysilicone composition that is stable to epoxide-mediated crosslinking both during and after a hydrosilation reaction, as well as to a method for stabilizing olefin epoxides and epoxysilicones in the presence of a hydrosilation catalyst and SiH-functional group.

The hydrosilation reaction of unsaturated epoxides to SiH-functionalized silicone polymers has long been recognized as an elegant and convenient route to the manufacture of functionalized silicone materials. Epoxysilicone polymers are conveniently manufactured through the hydrosilation reaction between a SiH-functionalized silicone and olefin epoxide. The general hydrosilation reaction for silanes can be expressed as

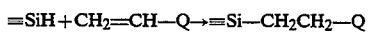
≡SiH+CH₂=CH—Q→≡Si—CH₂CH₂—Q and the general hydrosilation reaction for siloxanes can be expressed as

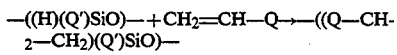
—((H)(Q')SiO)—+CH₂=CH—Q→—((Q—CH 2—CH₂)(Q')SiO)— where Q and Q' represent an organic radical. These reactions, as well as hydrosilation reactions in general, are known to be catalyzed by platinum compounds. However, as disclosed in commonly assigned U.S. patent application Ser. No. 07/473,802, filed Feb. 2nd, 1990, it has become apparent that the same platinum reagents used in the catalysis of the hydrosilation reaction to generate heterocyclic epoxy-functionalized silicones also promotes a highly undesirable epoxy ring-opening reaction. This latter reaction results in crosslinking and premature gelling of an epoxysilicone in the presence of SiH groups and the platinum hydrosilation catalyst species. The oxirane ring-opening side reaction is particularly troublesome at the elevated temperatures encountered during normal processing, but also serves to reduce the shelf life of epoxy-functionalized silicone products.

In order to partially circumvent the gelling caused by epoxide ring-opening during the hydrosilation reaction, epoxysilicone fluids have heretofore been produced using careful control of batch temperature and olefin-epoxide feed rate during the addition reaction, and by use of low levels of mercaptans to deactivate the platinum catalyst after the completion of the hydrosilation reaction. There remains, however, the possibility that ring-opening polymerization will occur during any given batch synthesis.

Rhodium compounds are also known to catalyze the hydrosilation reaction between an SiH-functional silane or siloxane and an ethylenically unsaturated organic radicals. For example, see generally J. F. Harrod and A. J. Chalk, in "Organic Syntheses via Metal Carbonyls", Vol. 2, I. Wender and P. Pino, eds., pp. 685-687, John Wiley & Sons, New York; and J. L.Speier, Advances in Organometallic Chemistry, Vol. 17, 407 (1979). Additionally, commonly assigned U.S. Patent application entitled "Preparation of Epoxysilicon Compounds using Rhodium Catalysts", (Crivello and Fan) U.S. patent application Ser. No. 07/583,524 filed Sep. 17, 1990, Now U.S. Pat. No. 5,169,962 issued Dec. 8, 1992, discloses several rhodium catalysts suitable for use in the particular hydrosilation reaction between SiH—functional silanes or siloxanes and olefin epoxides. Also, U.S. Pat. No. 4,946,818 discloses that a rhodium colloid made by the reaction between rhodium chloride and certain silicon hydrides is an effective hydrosilation catalyst, and U.S. Pat. No. 3,928,629 discloses a process in which a rhodium sulfide or rhodium carbonyl complex is used as catalyst for organohydrogen polysiloxane-based release coatings.

Hydrosilation reactions between olefin epoxides and organohydrogensiloxanes catalyzed with platinum metal complexes containing rhodium have also been described. Reference is made to U.S. Pat. No. 4,279,717 (Eckberg) and to commonly assigned U.S. patent application Ser. Nos. 07/332,646, filed Apr. 3, 1989, and 07/473,802, filed Feb. 2, 1990.

A tertiary amine stabilizer for use with epoxy-functional silanes and siloxanes has also been previously described in the above-mentioned, commonly assigned U.S. Patent application of Crivello and Fan. In that case, a tertiary amine is added following the completion of the addition of olefin epoxide to an SiH-functionalized silicone, but prior to the stripping of volatiles from the reaction product. Thus, the tertiary amine stabilizer is not present during the addition reaction itself, such that epoxy crosslinking promoted by the elevated temperature of the addition reaction often cannot be avoided.

Due to the undesirable ring opening reaction during the hydrosilation addition, the reproducibility of the products obtained, particularly with respect to viscosity, has heretofore been less than optimal. There thus exists a need in the epoxysilicone industry for a hydrosilation reaction for the addition of epoxy-functionalized unsaturated compounds to SiH-functionalized silanes and siloxanes, in which the epoxy-ring opening is greatly suppressed or eliminated. Preferably, the epoxy ring-opening reaction would be eliminated throughout the course of the addition reaction rather than only afterwards. In such a preferred scenario, the batch-to-batch reproducibility of the end-product, as well as its shelf-life, would be substantially increased. All patents and references described herein are incorporated by reference.

SUMMARY OF THE INVENTION

The invention provides for improved hydrosilation syntheses of epoxysilicones wherein certain rhodium and platinum sulfide compounds are employed as catalyst in the presence of a tertiary amine stabilizer, the latter of which is included in a reaction mixture prior to the initiation of the addition reaction. The process of the invention effectively prevents the premature gelling of epoxysilicone materials during both the addition reaction and subsequent processing and storage. Suitable hydrosilation catalysts for practicing the process of the invention include compounds of the formulas $RhX_3(R^1_2S)_3$ and $PtX_2(R^1_2S)_2$, where X is a halogen other that $F^-$, and $R^1$ is an alkyl, aryl, alkaryl or aralkyl, substituted or unsubstituted organic radical, preferably $C_{(1-30)}$ alkyl, and most preferably n-butyl or ethyl radical. Suitable tertiary amine stabilizers in the process of the invention are those of the formula $R^1_3N$, wherein $R^1$ has the above-stated meaning, and where each $R^1$ group may be the same or different than the others. A preferred tertiary amine stabilizer in the process of the invention is methyldicocoamine, $CH_3(C_{18}H_{37})_2N$. The invention also provides for a composition comprising olefin epoxides, epoxysilicones and SiH-functional silanes or siloxanes, that incorporates a tertiary amine to prevent the catalysis of oxirane ring opening reactions in the presence of SiH groups and hydrosilation catalyst. The discovery of the present invention makes possible the production of highly reactive epoxysilicone fluids such as $M^eM^e$ and $(D^e)_4$, which were heretofore difficult to make with previously existing technology due to the strong tendency of these compounds to undergo acid-type, thermally induced and epoxy-mediated crosslinking during the addition reaction.

DETAILED DESCRIPTION OF THE INVENTION

Platinum catalysts in the presence of SiH-functionalized molecules and epoxy-functional silicones, generally promote a thermally induced oxirane ring opening reaction of the epoxide, which thereby prematurely initiates a crosslinking reaction during the hydrosilation addition reaction. One object of the present invention is to provide a system wherein the premature crosslinking of epoxysilicones due to the opening of oxirane rings is greatly suppressed or even eliminated throughout the course of both the addition reaction and subsequent processing steps. Although tertiary amines are known to stabilize the products of the reaction when added after the addition was completed, it was an unexpected finding that a tertiary amine stabilizer was useful to this same end during the addition reaction itself, provided that certain rhodium or platinum catalysts are used to catalyze the addition reaction. This finding was surprising particularly since tertiary amines, being basic in nature, generally would be expected to poison precious-metal catalysts typical of those used in for the hydrosilation reaction. Previously, this poisoning of the catalyst was one of the very reasons that tertiary amine stabilizers were added after the addition reaction was completed. It was equally unexpected that only sulfur-containing rhodium and platinum catalysts are active in the presence of tertiary amines, while other well known hydrosilation catalysts, for example phosphorus-containing rhodium catalysts, are poisoned by the presence of the stabilizer. Thus, as exemplified below, the proposition that tertiary amines poison hydrosilation catalysts likely remains generally true.

The process of the invention is most generally the reaction between an SiH-functional silane or siloxane and an olefin epoxide in the presence of a tertiary amine stabilizer. As would be readily recognized in the art, there are many silanes, polysiloxanes and their derivatives that are suitable for use in the process and product of the present invention; the only general limitation being that there be at least one functional SiH group present on the molecule, such that the silicone is capable of undergoing the hydrosilation addition reaction. For example, simple polysiloxanes of the general formula $$R^2_3SiO(R^3_2SiO)_nSiOR^2_3$$

where $R^2$ and $R^3$ are, individually, hydrogen, or a substituted or unsubstituted alkyl group having from about 1 to 12, and preferably about 1 to 5 carbons; with the provision that at least two $R^2$ or $R^3$ groups are hydrogen; and n is from about 4 to about 1000, preferably from about 1 to about 400 are suitable for use in the product and process of the invention. Throughout this disclosure and in the claims appended hereto, by use of the term "substituted" it is meant an organic radical having chloro, bromo, iodo, cyano, carboxy, mercapto, hydroxy, thio, amino, nitro or other groups contained therein, as known in the art. Additionally, heterocyclic and aromatic heterocyclic organic radicals such as pyridyl, thiophenyl, pyranyl, and other as known in the art are also meant to be encompassed in the definition of "substituted" organic radicals. The process of the invention is additionally useful in the preparation of silicone-organic copolymers, terpolymers, etc. as are known in the art, provided that these polymers not be so acidic as to effectively neutralize the action of the stabilizer.

Suitable olefin epoxides for use in the process and product of the reaction are limoneneoxide, 4-vinylcyclohexene oxide (VCHO), allylglycidylether, glycidylacrylate, 7-epoxy-1-octene, vinylnorborene monoxide, dicyclopentyldiene monoxide and the like. Preferably the unsaturation in the olefin epoxides is terminally located on an alkyl chain, as such bonds have been found to be more reactive in the hydrosilation reaction than those located internally. Most preferably, 4-vinylcyclohexeneoxide is employed as the olefin epoxide in the practice of the present invention.

Suitable catalysts for use in the process and product of the reaction are rhodium or platinum sulfide compounds of the general formula $$RhX_3(R^1_2S)_3$$

and $$PtX_2(R^1_2S)_2$$

where X is a halogen other than $F^-$ and $R^1$ is $C_{(1-30)}$ alkyl, aryl, alkaryl or aralkyl, preferably $C_{(1-20)}$ alkyl and most preferably $C_{(1-10)}$ alkyl and may be substituted or unsubstituted. Preferred in the product and process of the invention is the use of $RhCl_3[(CH_3(CH_2)_3)_2S]_3$ or $PtCl_2[(CH_3CH_2)_2S]_2$ or a mixture thereof.

Other common hydrosilation catalysts which are not operative in the present invention include Wilkinson's catalyst $(RhCl((C_6H_5)_3P)_3)$, Lamoreaux's catalyst $(H_2PtCl_6$ in octyl alcohol as described in U.S. Pat. No.

3,220,972), Speier's catalyst (chloroplatinic acid) and Karlstedt's catalyst (platinum-silicone complex containing less than 0.1 gram atom of halogen per gram atom of platinum). These catalysts are apparently poisoned by a tertiary amine.

Sulfur containing rhodium catalysts operative in the invention and the method of their preparation are disclosed in U.S. Pat. No. 3,828,629 (Chandra, et al.). As discussed in this reference, complexes of the formula $RhX_3(R_2S)_3$ in which the R groups are organic radicals that do not contain silicon can be prepared, for example, according to the disclosure in Jour. Chem. Soc. (A), (1971), 899. Complexes having this same general formula which contain silicon may be prepared by reacting together a rhodium halide $RhX_3$ and a silicon-containing sulphide $R_2S$, preferably in the presence of a polar solvent.

The amount of catalyst added in the process of the invention is generally that which will affect a complete hydrosilation reaction between a organohydrogen siloxane and olefin epoxide in a suitable time, for example, in less than 2 hours. In general, the catalyst is best used in an amount of from about 0.1 to about 50 parts per million, preferably from about 1 to about 20 parts per million, and most preferably from about 2 to about 5 parts per million, each by weight of precious metal as compared to the weight of the curable composition.

In the process and product of the instant invention, a stabilizer is used to prevent the temperature-induced oxirane ring opening reaction. In general, stabilizers useful in the practice of the invention are basic compounds. Three criteria in the choice of suitable stabilizers are that the compound prevent acid-type epoxide ring opening, not poison the hydrosilation catalyst, and that the stabilizer not be volatile or thermally unstable. This latter property is desirable since it is generally useful for the stabilizer to remain active after step of stripping volatiles from the reaction mixture. It has been found that tertiary amines are particularly useful stabilizers for practice of the invention. Suitable tertiary amines include substituted or unsubstituted trialkylamines, triarylamines, alkarylamines, aralkylamines and mixed amines comprising more than one of these substituents, for example diethylphenylamine, diphenylethylamine, etc.. A preferred tertiary amine is methyldicocoamine, $CH_3(C_{18}H_{37})_2N$.

In the product and process of the invention, the tertiary amine stabilizer is added to an Si-H functional silane or siloxane fluid before the addition of catalyst and subsequent addition of olefin epoxide. In this case, acid-type, thermally induced oxirane ring opening is prevented throughout the hydrosilation addition reaction. Also, as the preferred tertiary amine of the present invention is not volatile, its stabilizing action remains effective throughout subsequent processing steps, particularly the step of stripping volatiles from the reaction product. Moreover, the preferred tertiary amine of the present invention is thermally stable and compatible with storage of the Si-functional silicones, so that batches of SiH-containing silane and siloxane fluids can be pre-mixed with the stabilizer in large scale for subsequent use in the future as dictated by need.

For use in the present invention, tertiary amine stabilizer is added to a mix of SiH-functionalized siloxane and olefin epoxide at a concentration sufficient to inhibit gelation, as is readily determinable by those of skill in the art. In general, the lowest level of tertiary amine which is effective in preventing gelation is the choice amount. Tertiary amine stabilizer present at a concentration of from about 10 to about 1000 ppm with respect to the weight of the curable composition, is sufficient to practice the invention. Preferably, tertiary amines are used at a concentration of about 20 to about 500 ppm and most preferably from about 50 to about 200 ppm, both as compared to the weight of the curable composition.

In practicing the process of the present invention, an SiH-functional silane, siloxane or suitable SiH-functionalized derivative is conveniently mixed with the tertiary amine stabilizer, after which is added a suitable rhodium or platinum sulfide hydrosilation catalyst, such as the preferred tris(di-n-butylsulfide) rhodium trichloride of bis(diethylsulfide) platinum dichloride. The silane or siloxane is added from about 20 to about 95 parts, by weight, whereas the olefin epoxide is added in from about 80 to about 5 parts by weight. The hydrosilation reaction is then conveniently initiated by the addition of olefin epoxide at mildly elevated temperatures. Preferably, the olefin epoxide is added slowly, with mixing, to prevent high local concentration of epoxide and relatively low local concentration of stabilizer from developing in the batch. Shortly after the addition of epoxide, a large exotherm is quickly achieved. It has been found that at exotherms up to even 180° C. to about 190° C. are achieved in the process of the invention without any detectable gelling of the fluid.

Following the completion of the hydrosilation reaction, the reaction mixture is devolatilized to remove excess olefin epoxide and low molecular weight linear and cyclic siloxane light ends. Devolatization is preferably accomplished in vacuo and at an elevated temperature. The temperature of the so-called "stripping" step in the process of the invention is at between about 100° C. and about 250° C. Preferably this heating step is from between about 125° C. and about 225° C., and most preferably the stripping step is performed at between about 150° C. and about 200° C. The pressure of the stripping step is generally preferred to be below atmospheric, as such reduced pressure aids in the release of volatile molecules from the epoxysilicone reaction product. Thus the lower the pressure that can be conveniently obtained, the better. Preferred in the stripping step in the process of the invention are pressures less than about 25 torr. Most preferred for this process step are pressures below about 10 torr. A rotary evaporator, used as known in the art, is conveniently employed in the devolatization step of the process of the invention. "Thin film" or "wiped film" evaporators are also conveniently employed to efficiently remove light ends in commercial processing.

The epoxysilicones produced by the process of the invention can be conveniently applied to a substrates including paper, metal, foil, polyethylene coated Kraft paper (PEK), supercalendered Kraft paper (SCK), polyethylene films, polypropylene films and polyester films. In general, coating can be applied to these substrates at the desired thickness as is known in the art. For example, compositions of the invention are readily applicable by doctor blade in a laboratory setting. For applications as a release coating, the epoxysilicone compositions are applied at a thickness of between about 0.1 mil and 10 mils; it is also convenient to refer to such coatings in terms of "coat weights", typically 1 g/m². Coatings can thereafter be cured thermally, as exemplified below and known in the art.

Due to the highly controllable conditions of the reaction and efficient stabilization of the product of the invention, many heretofore difficult epoxy-functional siloxanes can be easily and routinely prepared. For example, compounds such as $M^\epsilon M^\epsilon$ and $(D^\epsilon)_4$ which are normally difficult to prepare due to their high reactivity, are easily prepared by the process of the invention. Additionally, as exemplified below, the incorporation of a tertiary amine stabilizer in the reaction mixture prior to the addition reaction can significantly lower the viscosity of the resultant fluid as compared to reactions where stabilizer is added after the addition reaction, as the oxirane ring opening is greatly suppressed or eliminated in the former case but not in the latter. The process of the invention thus makes possible the heretofore unavailable ability to manufacture highly reproducible epoxysilicone fluids, particularly with respect to viscosity, thereby greatly reducing the batch-to-batch inconsistencies previously associated with the production epoxysilicones.

Experimental

Unless otherwise indicated, all resins and catalysts are available from General Electric Silicones, Waterford, N.Y. In the shorthand notation of polymer structure herein, the following apply:

M represents $(CH_3)_3SiO_{0.5}$;

$M^\epsilon$ represents 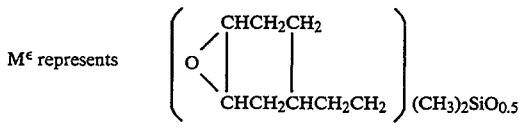 $(CH_3)_2SiO_{0.5}$ $M^H$ represents $(CH_3)_2HSiO$;

$M^{Vi}$ represents $(CH_2{=}CH)(CH_3)_2SiO_{0.5}$;

D represents $(CH_3)_2SiO$;

D' represents $-OSi(CH_3)_2CH_2CH_2-$;

$D^\epsilon$ represents 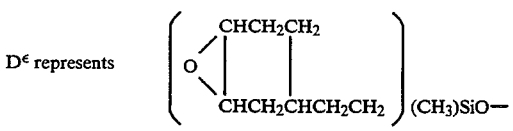 $(CH_3)SiO-$ $D^H$ represents $(CH_3)(H)SiO$; and,

EXAMPLE 1

Two hundred grams of an 18 cstk viscosity silicone fluid (grade 88405), of approximate structure $MD_{15}D^H_4M$, 0.19% H, were charged to a 1 liter flask. 0.025 grams of methyldicocoamine, $CH_3(C_{18}H_{37})_2N$, were added, followed by 0.6 grams of a 2% solution of tris(triphenylphosphine) rhodium trichloride, also known as Wilkinson's catalyst, in 4-vinylcyclohexene oxide (VCHO). This mixture was agitated at 115° C. as 50 grams VCHO were added dropwise. No exotherm or other overt evidence of reaction was detected at this time, and after a 2 hour hold at this temperature, FTIR examination of the reaction mixture, monitoring the strong SiH absorbance at 2200 cm$^{-1}$, confirmed that no loss of SiH had occurred. At this point, 0.1 gram of a solution of $RhCl_3[(CH_3(CH_2)_3)_2S]_3$ in ethanol containing 1.36% rhodium, by weight, was added to the reaction mixture. An immediate sharp exothermic response took place, with the batch temperature rising to about 180° C. within a few seconds of the addition of catalyst. Under these conditions, the highly reactive epoxysilicone formed in the absence of any dispersing medium would have quickly crosslinked to form a gel had the tertiary amine stabilizer not been present. The mixture was subsequently stripped of light ends in vacuo at 160° C. for one hour. 225 grams of a 87.8 cstk fluid product was obtained. This product had a refractive index of $n_D{}^{25} = 1.4233$ and a solids content per 150° C., 45 minute weight loss test of 97.5%.

Comparative Example 2

An epoxysilicone product was made as in Example 1 using the same ethanolic solution of $Rh[(CH_3(CH_2)_3)_2S]_3$, with the exception that the tertiary amine was not present in the mixture at the time of the VCHO feed. VCHO addition was at 110° C. followed by a two hour hold at that temperature to give a complete reaction of SiH, as judged by FTIR. 0.025 grams of methyldicocoamine stabilizer was then introduced into the mixture, after which the mixture was devolatilized as in Example 1. This reaction protocol yielded 225 grams of a 97 cstk viscosity fluid, with a refractive index $n_D{}^{25} = 1.4235$. Solid content was measured at 97.4%. It should be noted that the epoxysilicone product of Comparative Example 2 is 10% higher in viscosity than the product of Example 1.

EXAMPLE 3

All attempts at solvent-free synthesis as above using non-sulfur containing platinum catalysts and in the absence of any inert dispersing medium resulted in gelation during the VCHO feed into the reaction mixture. This was even true when the temperature of the mixture was kept at 75° C. or less.

EXAMPLE 4

256 g (2.06 moles) of 4-vinylcyclohexeneoxide were weighed into a 2 liter flask with 400 grams toluene, 0.04 grams $CH_3(C_{18}H_{37})_2N$ and sufficient $RhCl_3[(CH_3(CH_2)_3)_2S]_3$ to furnish 2 ppm rhodium in the complete reaction mixture. The agitating solution was brought to 100° C., when 134 grams (1.00 mole) of 1,1,3,3-tetramethyldisiloxane ($M^H M^H$) were added dropwise over a 30 minute period. Following the addition, reflux temperature was raised to 115° C. (that of toluene), indicating that the disiloxane (bp 72° C.) had completely reacted with VCHO. After 2 hours hold at 115° C., FTIR analysis detected no unreacted SiH. Toluene and excess VCHO were stripped off in vacuo, leaving 375 grams yield (98% of theoretical) of 23.4 cstk mobile fluid product, refractive index = 1.4740 (25° C.) vs. literature value = 1.4731 (E. P. Plueddemann et al., J. Amer. Chem. Soc. 81, 2632 (1959)). This material can be represented as $M^\epsilon M^\epsilon$,

and has been shown to be an extremely reactive diepoxy monomer (Crivello and Lee, Proceedings of A.C.S. Division of Polymeric Materials: Science and Engineering, Vol 60, pg 217, (1989); also Eckberg and Riding, ibid., pg 222).

Comparative Example 5

The synthesis of $M^eM^e$ was carried out as described in Example 4, except that tris(triphenylphosphine) rhodium (I) chloride (Wilkinson's catalyst) was substituted for the dibutylsulfide complex, and the tertiary amine stabilizer $(CH_3)(C_{18}H_{37})_2N$ was only added to the reaction mixture after all SiH had reacted. Removal of solvent and excess VCHO afforded a good yield of a 98 cstk fluid product, $N_D^{25}=1.4750$. It should be emphasized that this material is 4 times the viscosity of the product described in Example 4, indicating that epoxy crosslinking had occurred during the synthesis.

Comparative Example 6

Several attempts to synthesize $M^eM^e$ using platinum hydrosilation catalysts were carried out via addition of 1 mole $M^HM^H$ to 2 moles VCHO in toluene at 60°–80° C., using the Karstedt platinum catalyst at a concentration of 5 ppm Pt. The reaction proved to be unpredictable. In about half of the syntheses, gelation occurred very suddenly midway through the disiloxane additions, accompanied by vigorous and uncontrollable exothermic response. Isolable products were obtained in some of these experiments, with viscosities ranging from 70 to 1000 cstk. It is apparent that the highly reactive diepoxydisiloxane, $M^eM^e$, cannot be reliably nor reproducibly processed using standard platinum hydrosilation catalysts.

EXAMPLE 7

A low viscosity liquid silicone resin, approximate stoichiometry $M_2^HQ$, where "Q"=—$SiO_{4/2}$—, 1.0 wt % H (in the form of $H(CH_3)_2SiO_{\frac{1}{2}}$—), designated 88104, is a highly reactive crosslinker useful for certain thermal two part RTV applications. Attempts to produce the addition product of this material with stoichiometric amounts of VCHO using non-stabilized platinum catalysts such as the Karstedt or Lamoreaux catalyst always ended in rapid onset of gelation accompanied by uncontrollable exotherms, regardless of how the addition was carried out, or how much solvent diluent was present, and even at addition temperatures less than 50° C. We then carried out the synthesis using an alkylsulfide platinum complex in the presence of the tertiary amine stabilizer, as follows:

100 g of $M_2^HQ$ resin, 1.0 mole H, were weighed into a 2 liter flask with 0.025 grams $(CH_3)(C_{18}H_{37})_2N$, 200 grams toluene, and 0.25 grams of a 1% solution of dichlorobis(diethylsulfide) platinum (II) catalyst in methylenechloride. The solution was brought to 100° C., when 136 grams VCHO (1.10 mole) were added dropwise over a 60 minute period. An exothermic response maintained the reaction mixture at 115° C. reflux without external heating shortly after commencing this addition. Following the VCHO feed, no SiH peak was detectable in the infrared spectrum of the product. Removal of solvents and excess VCHO afforded 202 grams (90% yield) of a viscous fluid product, 8000 cps viscosity, $N_D^{25}=1.4806$. This product was quite miscible with 1 wt percent (4-octyloxyphenyl)(phenyl)iodonium hexafluoroantimonate photocatalyst, and the photocatalyzed mixture rapidly cured to a hard, glossy 2 mil coating on exposure to only 16 mJ/cm² UV light when coated on a polyethylene sheet. Obviously, the very high epoxy content of this material renders it extremely reactive as well as miscible with the iodonium photocatalyst.

It is understood that various other modifications will be apparent to and can be readily made by those skilled in the art without departing from the scope and spirit of this invention. Accordingly, it is not intended that the scope of the claims appended hereto be limited to the description set forth above but rather that the claims be construed as encompassing all of the features of patentable novelty which reside in the present invention, including all features which would be treated as equivalents thereof by those skilled in the art to which the invention pertains.

What is claimed is:

1. A composition comprising an SiH-containing silane or siloxane, an olefin epoxide, a rhodium or platinum sulfide of the formula $RhX_3(R^1_2S)_3$ or $PtX_2(R^1_2S)_2$, where X is a halogen other than $F^-$, and $R^1$ is an independently substituted or unsubstituted $C_{1-30}$ alkyl, aryl, alkaryl or aralkyl, and a tertiary amine, wherein said tertiary amine is used at a concentration of from about 10 to about 1000 part per million with respect to the weight of said composition.

2. The composition set forth in claim 1, wherein said tertiary amine is selected from the group consisting of substituted or unsubstituted trialkylamines, triarylamines, alkarylamines, aralkylamines and mixed tertiary amines.

3. The composition set forth in claim 2, wherein said tertiary amine is methyldicocoamine.

4. The composition set forth in claim 1, wherein said olefin epoxide is selected from the group consisting of limoneneoxide, 4-vinylcyclohexene oxide, allylglycidylether, glycidylacrylate, 7-epoxy-1-octene, vinylnorborene monoxide, and dicyclopentyldiene monoxide.

5. The composition set forth in claim 4, wherein said tertiary amine is selected from the group consisting of substituted or unsubstituted trialkylamines, triarylamines, alkarylamines, aralkylamines and mixed tertiary amines.

6. A method of preventing crosslinking of epoxy groups in a hydrosilation addition reaction comprising the steps of:

(a) preparing a first composition comprising an SiH-containing silane or siloxane and a rhodium or platinum sulfide complex of the formula $RhX_3(R^1_2S)_3$ or $PtX_2(R^1_2S)_2$, where X is a halogen other than $F^-$, and each $R^1$ group is independently substituted or unsubstituted $C_{1-30}$ alkyl, aryl, alkaryl, or aralkyl;

(b) adding a tertiary amine to said first composition prior to initiation of a hydrosilation addition reaction between said SiH-containing silane or siloxane and subsequently adding olefin epoxide and whereby the hydrosilation is initiated.

7. The method as set forth in claim 6, wherein in step (b) said tertiary amine is selected from the group consisting of trialkylamines, triarylamines, alkarylamines, aralkylamines and mixed tertiary amines.

8. The method as set forth in claim 7, wherein in step (b) said tertiary amine is methyldicocoamine.

9. The method as set forth in claim 6, wherein in step (b) said olefin epoxide is selected from the group consisting of limoneneoxide, 4-vinylcyclohexene oxide, allylglycidylether, glycidylacrylate, 7-epoxy-1-octene, vinylnorborene monoxide, and dicyclopentyldiene monoxide.

* * * * *